United States Patent
Mante et al.

(10) Patent No.: US 12,013,376 B2
(45) Date of Patent: Jun. 18, 2024

(54) SENSOR FOR CONCRETE STATIC MODULUS OF ELASTICITY IN SITU MEASUREMENT

(71) Applicant: Lafayette College, Easton, PA (US)

(72) Inventors: David M. Mante, Easton, PA (US); Zachary W. Coleman, Brodheadsville, PA (US); Aaron Buck, Lebanon, NH (US)

(73) Assignee: Lafayette College, Easton, PA (US)

( * ) Notice: Subject to any disclaimer, the term of this patent is extended or adjusted under 35 U.S.C. 154(b) by 310 days.

(21) Appl. No.: 17/655,924

(22) Filed: Mar. 22, 2022

(65) Prior Publication Data

US 2022/0299410 A1   Sep. 22, 2022

Related U.S. Application Data

(60) Provisional application No. 63/200,676, filed on Mar. 22, 2021.

(51) Int. Cl.
   *G01N 3/08* (2006.01)
   *G01N 3/06* (2006.01)
   (Continued)

(52) U.S. Cl.
   CPC ............. *G01N 3/08* (2013.01); *G01N 3/066* (2013.01); *G01N 3/068* (2013.01); *G01N 33/383* (2013.01);
   (Continued)

(58) Field of Classification Search
   CPC .......... G01N 3/08; G01N 3/066; G01N 3/068; G01N 33/383; G01N 2203/0019;
   (Continued)

(56) References Cited

U.S. PATENT DOCUMENTS

| | | | |
|---|---|---|---|
| 2013/0192382 A1* | 8/2013 | Bois | G01N 33/383 |
| | | | 73/803 |
| 2013/0228019 A1* | 9/2013 | Meadows | G01N 3/08 |
| | | | 73/818 |
| 2014/0007695 A1* | 1/2014 | Darbe | G01N 3/12 |
| | | | 73/803 |

FOREIGN PATENT DOCUMENTS

| | | | |
|---|---|---|---|
| CN | 205607747 U | * 9/2016 | |
| CN | 110208096 A | * 9/2019 | G01B 11/16 |

(Continued)

OTHER PUBLICATIONS

Mante et al., "In Situ Measurement of Concrete Static Modulus of Elasticity: Proof of Concept Implementation", Research in Nondestructive Evaluation, Jul. 24, 2021, vol. 32, Nos. 3-4, pp. 160-176,<https://www.tandfonline.com/doi/full/10.1080/09349847.2021.1948154>. (Year: 2021).*

(Continued)

*Primary Examiner* — Jonathan M Dunlap
(74) *Attorney, Agent, or Firm* — Vos-IP, LLC

(57) ABSTRACT

A sensor device for detecting static modulus of elasticity in situ comprising: top and bottom frame end plates, said top and bottom frame end plates connected by at least two frame side bars; a dry cavity connected to said top frame end plate comprising a piston, precompression mechanism, and piston transfer plate; a displacement measurement gauge extending from said dry cavity along a longitudinal axis of said sensor device having a first end in contact with said piston transfer plate and a second end in contact with a bottom inner face of said bottom frame end plate; and a top inner face connected to said piston transfer plate, wherein a portion of elastomeric material is positioned on said bottom and top inner faces, said elastomeric material positioned to prevent contact with either bottom or top inner faces except for a portion along the longitudinal axis of the displacement measurement gauge.

20 Claims, 11 Drawing Sheets

(51) Int. Cl.
*G01N 33/38* (2006.01)
*G01M 5/00* (2006.01)

(52) U.S. Cl.
CPC ........ *G01M 5/0041* (2013.01); *G01M 5/0066* (2013.01); *G01M 5/0091* (2013.01); *G01N 2203/0019* (2013.01); *G01N 2203/0076* (2013.01); *G01N 2203/0256* (2013.01); *G01N 2203/0617* (2013.01); *G01N 2203/0641* (2013.01)

(58) Field of Classification Search
CPC ... G01N 2203/0076; G01N 2203/0617; G01N 2203/0641; G01N 2203/0256; G01M 5/0066; G01M 5/0091; G01M 5/0041
See application file for complete search history.

(56) References Cited

FOREIGN PATENT DOCUMENTS

| CN | 111220452 A | * | 6/2020 | ............. G01N 15/08 |
|---|---|---|---|---|
| CN | 108562494 B | * | 8/2021 | ............. G01N 3/066 |

OTHER PUBLICATIONS

ACI Committee 209, Prediction of Creep, Shrinkage, and Temperature Effects in Concrete Structures (ACI 209R-92), Mar. 1, 1992.
ACI Committee 209, Guide for Modeling and Calculating Shrinkage and Creep of Concrete (ACI 209.2R-08), May 2008.
ACI Committee 228, Report on Nondestructive Test Methods for Evaluation of Concrete in Structures (ACI 228.2R-13), Jan. 26, 2015.
ACI Committee 318, Building Code Requirements for Structural Concrete (ACI 318-19), May 31, 2019.
ASTM International, ASTM C39: Standard Test Method for Compressive Strength of Cylindrical Concrete Specimens, Feb. 1, 2020.
ASTM International, ASTM C469: Standard Test Method for Static Modulus of Elasticity and Poisson's Ratio of Concrete in Compression, Mar. 1, 2014.
Geokon, Model 4200 Series Vibrating Wire Strain Gauges Instruction Manual, Nov. 8, 2019.
Mante, "Measuring Concrete Modulus of Elasticity", Concrete International, vol. 41, No. 8, Aug. 1, 2019, 28-33.

* cited by examiner

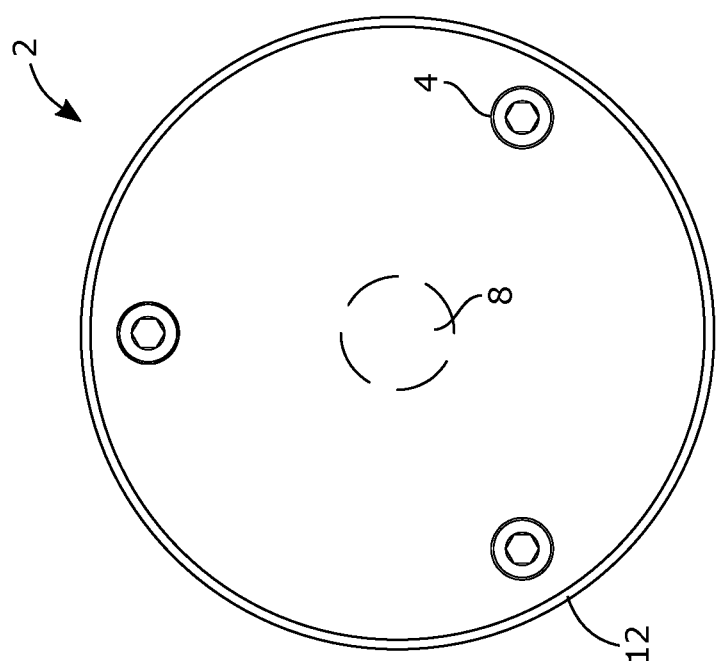
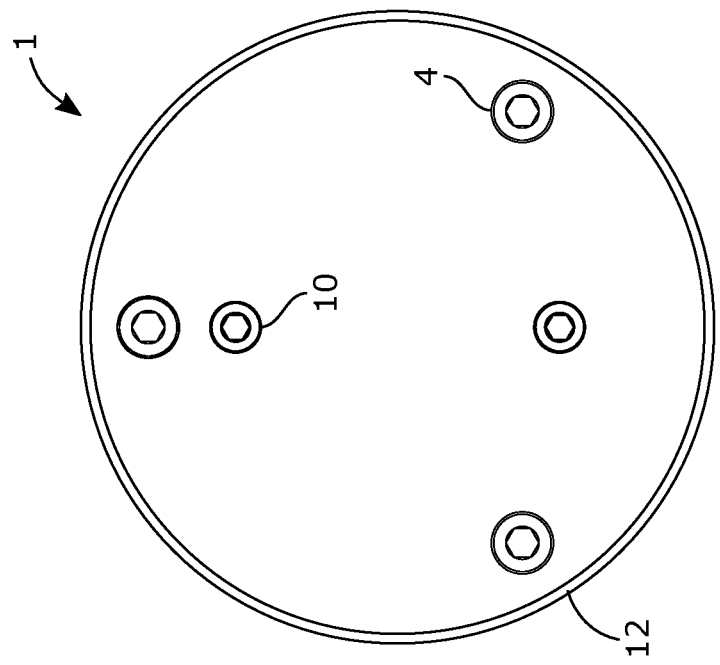

FIGURE 4
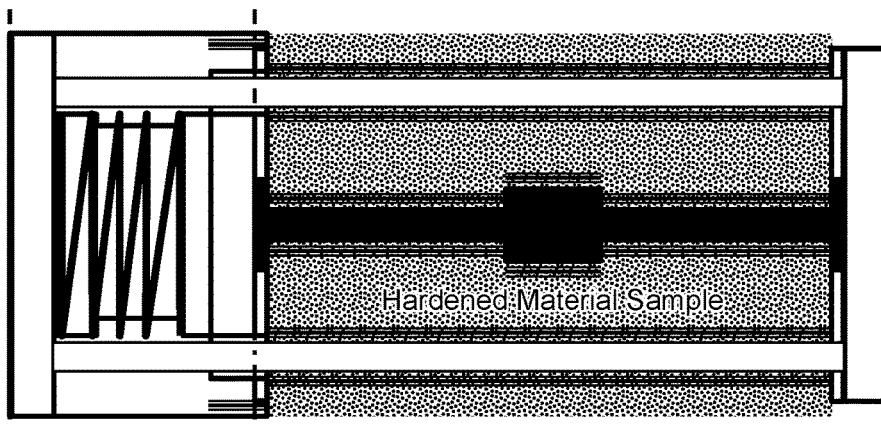
(a) Embedded sensor at $t = t_0$, before shrinkage, before activation
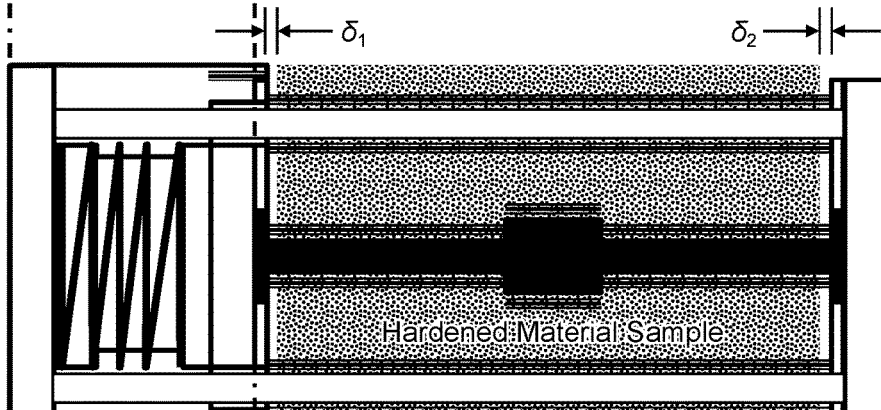
(b) Embedded sensor at $t = t_1$, after initial shrinkage, before piston activation
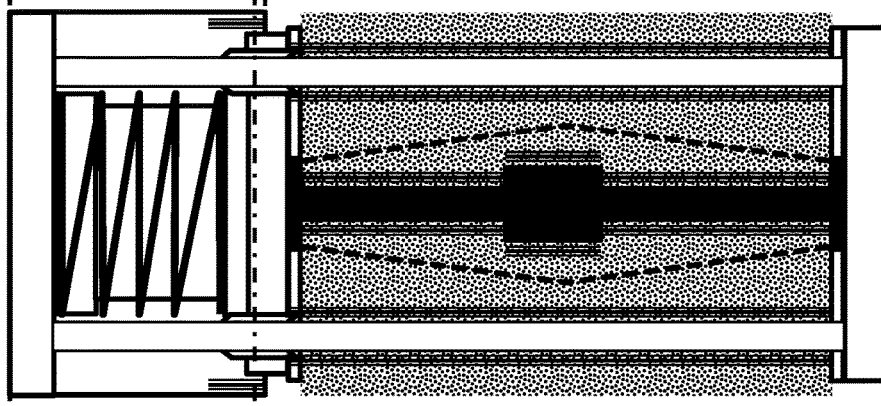
(c) Embedded sensor at $t = t_2$, after initial shrinkage, during piston activation

SENSOR FOR CONCRETE STATIC MODULUS OF ELASTICITY IN SITU MEASUREMENT

CROSS-REFERENCE TO RELATED APPLICATIONS

This application claims the benefit of U.S. Provisional Patent Application No. 63/200,676 filed on Mar. 22, 2021, with the United States Patent and Trademark Office, the contents of which are incorporated herein by reference in their entirety.

FIELD OF THE INVENTION

The application relates to a self-contained sensor capable of directly measuring in situ static concrete modulus of elasticity, and methods of using the same.

BACKGROUND OF THE INVENTION

The modulus of elasticity is a critical design parameter in building structures as it is a load-deformational relationship that serves as the foundational constitutive relationship for structural analysis and design. The static modulus of elasticity ($E_c$) is the ratio of applied stress to instantaneous strain within the linear portion of a loading curve as shown in FIG. 1. Typical values of $E_c$ for structural concrete applications range from 4,000,000 psi to 8,000,000 psi (reported to the nearest 50,000 psi). Concrete is assumed to exhibit relatively linear elastic behavior through the proportional limit, approximately 60% of its ultimate compressive strength, $f'_c$. Continued loading after the proportional limit results in the propagation of interfacial microcracking tending to cause the curved portion of the stress-strain relation.

Applied loads inducing stresses below the proportional limit, as shown in FIG. 1A, cause only elastic deformations that are fully recoverable upon unloading. Conversely, applied loads exceeding the proportional limit, as shown in FIG. 1B, cause both elastic deformations and permanent deformations that remain after unloading. To avoid permanent deformations under normal operating (service) conditions, structural concrete members are proportioned to ensure compressive stresses remain well below the proportional limit during intended use.

Devices to measure $E_c$ typically utilize requirements under ASTM C469 testing standards, which compress certain test cylinders of concrete that are intended as representative samples of the actual concrete utilized in a structural setting. However, numerous limitations exist for these test cylinders, including the fact that they can only be used once to test the $E_c$. Absent multiple test cylinders, determining when thresholds are met for $E_c$ within a structural element is based on approximations or single tests.

Applicant has created a novel sensor device capable of directly measuring in situ static concrete modulus of elasticity and corresponding methods of use of the same. This allows for repeated testing with a single sample, in situ, which, heretofore, was not possible.

SUMMARY OF THE INVENTION

In a preferred embodiment, a sensor device for detecting static modulus of elasticity in situ comprising: a top frame end plate and a bottom frame end plate, said top frame end plate and said bottom frame end plate connected by at least two frame side bars; a dry cavity connected to said top frame end plate, said dry cavity comprising a piston, and a piston transfer plate; a displacement measurement gauge extending from said dry cavity along a longitudinal axis of said sensor device, said displacement measurement gauge having a first end in contact with said piston transfer plate and a second end in contact with a bottom inner face of said bottom frame end plate; and a top inner face connected to said piston transfer plate, wherein a portion of elastomeric material is positioned on said bottom inner face and said top inner face, said elastomeric material positioned to prevent contact with either the bottom inner face or the top inner face except for a portion along the longitudinal axis of the displacement measurement gauge.

In a further embodiment, the sensor device further comprising a piston transfer component positioned between the piston and the piston transfer plate.

In a further embodiment, the sensor device further comprising a precompression mechanism. In a further embodiment, the sensor device wherein said precompression mechanism is selected from the group consisting of: a spring, a threaded adjuster, a hydraulic piston, and combinations thereof.

In a further embodiment, the sensor device wherein said piston is a pneumatic, hydraulic, or mechanically driven remote actuated piston.

In a further embodiment, the sensor device wherein the elastomeric material is selected from the group consisting of: neoprene, silicone, rubber, foam, a compressible polymer, and combinations thereof.

In a further embodiment, the sensor device wherein the displacement measurement gauge is a vibrating wire strain gauge or a fiber optic sensor.

In a further embodiment, the sensor device wherein the piston provides a known force when actuated.

In a further embodiment, the sensor device further comprising a debonding material positioned on said at least two frame side bars.

In a preferred embodiment, a method of detecting static modulus of elasticity in situ from a structural component sample comprising: (a) securing a sensor within a structural material; (b) securing within said sensor between a top frame end plate and a bottom frame end plate a displacement measurement gauge along a longitudinal axis of said top frame end plate and said bottom frame end plate; (c) activating a piston to a known force, said piston secured within a dry cavity attached to said top frame end plate wherein the piston extends from the top frame end plate to the bottom frame end plate along the longitudinal axis; (d) measuring displacement of said sensor from said displacement measurement gauge; and (e) calculating the static modulus of elasticity.

The method wherein the step of calculating the static modulus of elasticity further comprises: (e1) plotting the displacement of said sensor against a set of data from a database that correlates results of in situ testing with ASTM results for different concrete compositions and strength levels. In a further embodiment, the method wherein step (e1) comprises a Web-based data server, said Web-based data server automatically calculating and validating test data by comparing the test data to the set of data from a database.

In a further embodiment, the method wherein step (e) provides postprocessing of the displacement of said sensor as a curve of data, isolating a linear elastic portion of the curve, and calculating the modulus of elasticity.

In a further embodiment, the method comprising securing the sensor within a poured or cast structural material. In a further embodiment, the method wherein the structural material is hardened. In a further embodiment, the method wherein the structural material is concrete.

In a further embodiment, the method wherein the displacement measurement gauge is a vibrating wire strain gauge.

In a further embodiment, the method wherein the structural component sample is loaded to stress levels of between $0.0f_c$ and $0.6f_c$. In a further embodiment, the method wherein the structural component sample is loaded to stress levels of between $0.25f_c$ and $0.5\ f_c$. In a further embodiment, the method wherein measurement of in situ static concrete modulus of elasticity is repeatable within a single concrete sample.

BRIEF DESCRIPTION OF THE FIGURES

FIGS. 3A and 3B show a top and bottom profile of a sensor.

FIG. 4 details activation of the sensor device and measurements of changes.

DETAILED DESCRIPTION OF THE INVENTION

The subject matter of embodiments of the present invention is described here with specificity to meet statutory requirements, but this description is not necessarily intended to limit the scope of the claims. The claimed subject matter nay be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

As used in this specification and the appended claims, the singular forms "a," "an," and "the" include plural referents unless the context clearly indicates otherwise.

The term "about" means within 10% of a stated number.

As used herein a reference to modulus of elasticity, refers specifically to the static modulus of elasticity.

Described herein is a new sensor with potential application to a variety of materials with an initial linear elastic material deformational behavior. One such linear elastic material is concrete. The device described herein is in particular related to measuring the static modulus of elasticity in an in situ sample of concrete or other material which is placed as a fluid material, and eventually hardens or cures into a hardened material. This allows for calculation of the actual property of the concrete within a structural support and not an approximation based upon a cylindrical sample created under ASTM C469, which typically utilized a compressometer to apply a load a measure the shortening of the cylindrical sample under that load.

Instead, an elegant solution has been created, one that is formed within a concrete element and which can be measured directly in the structure and not simply a representative sample. The device comprises a sensor intended for direct measurement of in situ modulus of elasticity. The device must simultaneously apply a known force to a sample of material and measure the associated deformation. The initial linear nature of the stress-strain curve allows for computation of the modulus of elasticity by capturing a minimum of two points on the curve. It is expected that the precision of the modulus of elasticity estimate will increase as the separation between the uppermost and lowermost measurement points (the range) on the loading curve increases.

Figure 1:
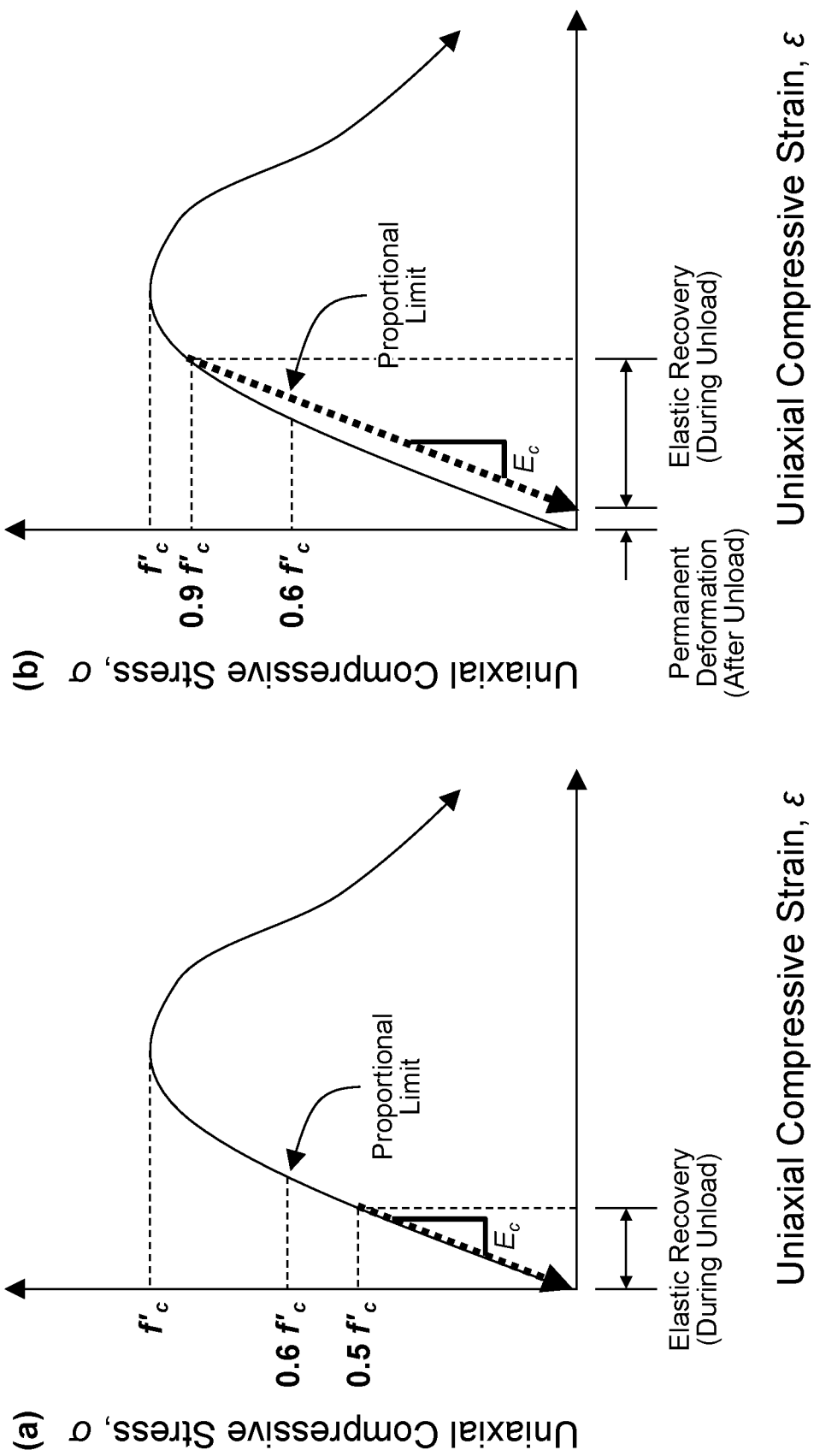
FIG. 1 details a concrete stress-strain curve and static modulus of elasticity.
Figure 2A:
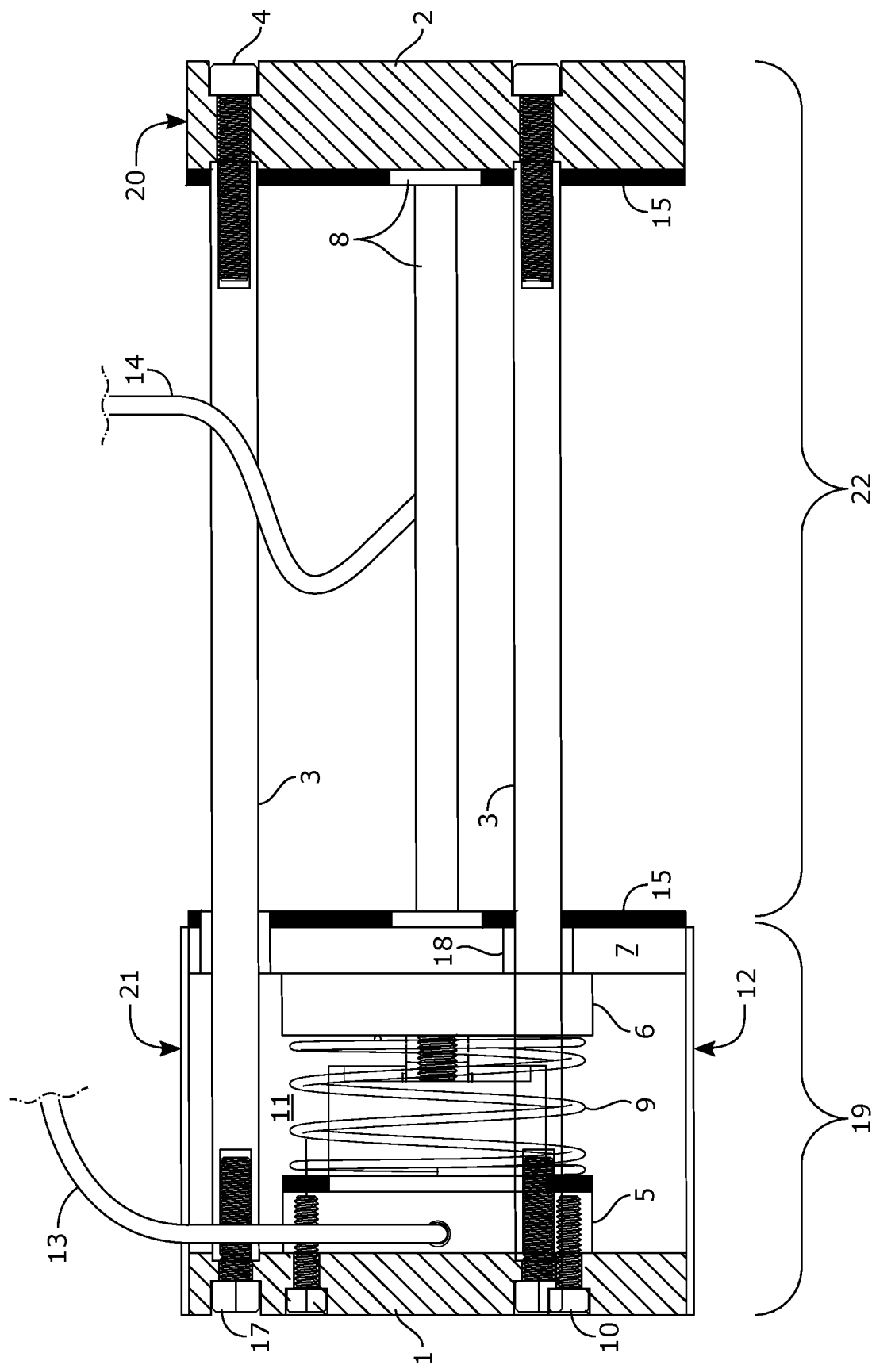
FIG. 2A details a sensor schematic utilizing a spring loading mechanism for precompression of the strain gage, while FIG. 2B utilizes an alternative embodiment relying on a set screw for precompression of the strain gage.
Figure 2B:
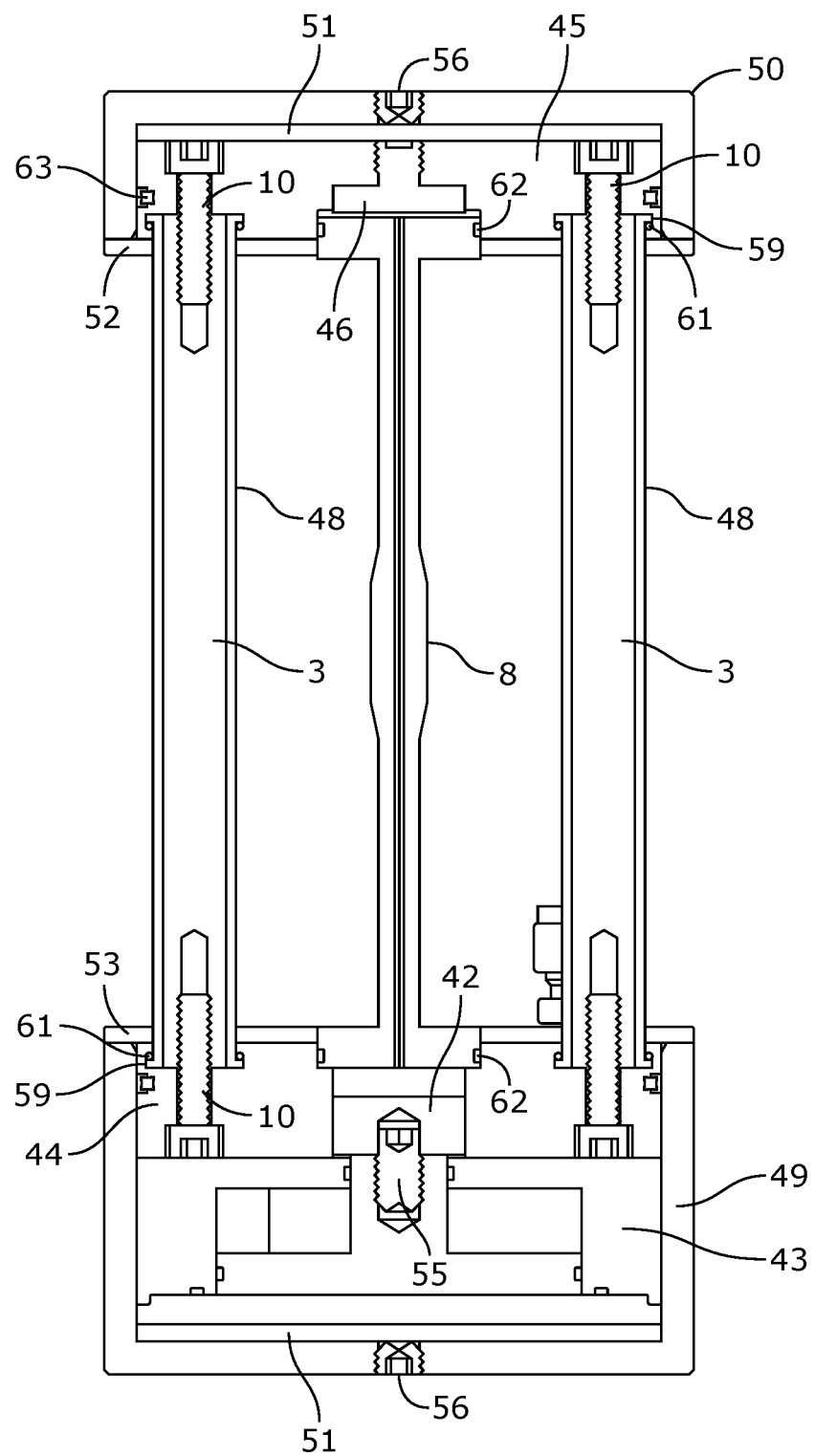

The sensor is more particularly detailed in FIGS. 2A and 2B. Beginning with FIG. 2A, which is a self-reacting frame comprised of a top frame end plate (1), a bottom frame end plate (2), which are connected with at least two frame side bars (3). The top frame end plate (1) and bottom frame end plate (2) are sized to resist frame stresses and minimize deformation and are defined to be secured within concrete. The at least two frame side bars (3) are sized to resist frame stresses, minimize deformation, and allow concrete or another material to encompass the frame. The top frame end plate (1) and bottom frame end plate (2) are secure to the at least two frame side bars (3) with threaded fasteners (10) which secure the components together. Typically, the frame end plates (1 and 2) comprise recesses (17) to receive the threaded fasteners (10). The size and length of the threaded fasteners depends on the appropriate size of the frame side bars (3). It is suitable to replace the threaded fasteners (10) with any other fastening mechanism, including but not limited to welding, press fit, rivet, or even single piece construction. Those of ordinary skill in the art recognize that there are numerous ways in which to connect two pieces, which will not diverge from the scope of the invention.

The device is intended for use within a structural material, for example concrete. However, while certain components are to be inundated with the structural material, other components remain free of the structural material. Thus, positioned adjacent to the top frame end plate (1) is a dry cavity (11), which is sealed from the structural component. The sealed cavity (11) comprises a piston assembly (19) comprising a precompression mechanism (9), a piston (5), a piston transfer component (6), and a piston transfer plate (7). The piston (5) is an appropriately sized pneumatic, hydraulic, or similar remote activated device that can be activated by wire or appropriately sized hose (13).

The dry cavity (11) is maintained in a sealed status by use of waterproofing or sealing side materials (12), which surround the dry cavity (11) on the sides and then sealing sleeves (18), which are positioned adjacent to the frame side bars (3) to prevent intrusion through these components. The sealing sleeves (18) must seal out moisture and the structural material to allow for the piston (5) to operate. The piston (5) operates by generating a known force to the piston transfer plate (7) and, ultimately, to the structural material sample within the gage and the displacement measurement gauge (8).

The displacement measurement gauge (8) is placed along the longitudinal axis of the device, and preferably placed along the center point of said axis between the piston transfer plate (7) and the bottom frame end plate (2) defined as the intrusion cavity (22). An example of the displacement measurement gauge (8) is a vibrating wire strain gauge, a fiber optic sensor, or another similar displacement measuring device. Attached to the displacement measurement gauge (8) is a sensor activation element (14), typically a wire or hose, that connects to the displacement measurement gauge (8) to allow for remote activation and/or collection of data from the displacement measurement gauge (8). In all cases, the sensor will be read with either a manual readout or automated data collection system. Captured data may then be input into a computer for postprocessing of the data received by the sensor.

The displacement measurement gauge (8) is intended to be embedded within a structural material, which is typically fluid in its first state before hardening or curing. Concrete is one of the key materials that fits into the category, but other composite or resin-based materials may also be poured and then cure and may utilize the device described herein. The displacement measurement gauge (8) being embedded within these materials allows for the structural material to fully surround the displacement measurement gauge (8) as well as the frame side bars (3), the top frame end plate (1), the bottom frame end plate (2), but does not allow intrusion of materials into the dry cavity (11). At each end of the intrusion cavity (22) is positioned a portion of elastomeric material (15), which is positioned on the bottom internal face (20) and the top internal face (21).

The purpose of the elastomeric material (15) on each end, is that it concentrates the forces applied to the structural material. In this manner, the intrusion cavity (22) is filled with the structural material. Because of the elastomeric material (15), when the piston transfer plate (7) is pressed forward, the forces and resistance provided by the structural material are concentrated along the longitudinal axis nearest the displacement measurement gauge (8). This is because, when the piston transfer plate (7) is pressed forward, the elastomeric material (15) is easily compressed (requiring a very small, known force to compress), as compared to the structural material. Thus, nearly all of the forces of the piston transfer plate (7) are concentrated on the small region of material, which is in contact with the central portion of the top internal face (21). By deliberately focusing the known piston force over a relatively small cross section of structural material, measurable shortening deformations can be achieved even for relatively stiff structural materials.

FIG. 2B provides an alternative embodiment, of the sensor device, and includes removal of the precompression mechanism (9) as a spring. Instead, the strain gauge (8) is held within counterbores on the top and bottom end plates, and a threaded screw-type adjustment mechanism (46) is used to precisely control the initial preload on the strain gauge and the gauge initial reading. Indeed, the threaded screw-type adjustment, allows for precise control of the pressure on the strain gauge. Furthermore, with the addition of certain compressible materials, the travel distance of the piston is able to overcome any shrinkage of the concrete as it hardens. Thus, in each case, the relative starting point of the sensor, just before a test, remains highly similar to allow for simple and reliable testing. In addition to the above, several O-rings seal the gauge ends from concrete test sample ingress during casting and provide for clean contact between rigid metal components comprising the gauge frame. Finally, the frame side bars (3) include a sleeve (48) to prevent intrusion or adhesion to the frame side bars (3) so as to eliminate error in measurements. This additional implementation simplifies details for waterproofing the dry cavity (11) and assembly, but it does not significantly change sensor operation.

Notably, the device of FIG. 2B provides for the same general features and same general mechanism of action as FIG. 2A. FIG. 2B comprises a strain gauge (8) as well as frame side bars (3). However, due to the slightly different arrangement, the features are labelled differently. Top (50) and bottom cups (49) are used to isolate the rigid frame components from surrounding concrete and allow the gauge to float inside with minimized friction during testing. The top (50) and bottom cups (49) and frame upright sleeves are cast in concrete, and in combination with foam cushions isolate and enable relative motion between the gauge frame and surrounding the test material. The top cup (50) contains an access plug (56), which provides user access to adjust initial strain gauge reading using preload adjustment (46) before installation. This adjustment, alone or in combination with the travel distance of the piston plate (42) provides for the same or similar status on the strain gauge as using the precompression spring in the prior embodiment. At the bottom portion, the set screw (55) can also be adjusted before inundation to set the device.

The top plate (45) and the base plate (44) are solid components in which the threaded fasteners (10) are secured therein. This provides a stable support for the frame side bars (3) to be attached. The top plate (45) and the base plate (44) are surrounded at each end under the top cup (50) and the bottom cup (49). A sealing ring (63) is positioned along the inner side of the top plate (45) and the base plate (44) to seal them against the top cap (50) and bottom cap (49). Within the top cup (50) and the bottom cup (49) is an outer foam cushion (51), which provide some give or float to the inundation of the concrete against into the device. Indeed, in combination with a corresponding set of inner foam cushions, the upper inner foam cushion (52) and a lower inner foam cushion (53), these cushions provide suitable give to the pressure of the concrete inundation into the device. Again, with the purpose of allowing the sensor to allow the rigid components of the sensor to float, allowing for a simple and elegant mechanism to test the strain on the concrete from a known force, applied through the piston plate (42) and measured by the strain gauge (8). Absent this float, the restriction from the concrete being secured to the device would prevent the repeatable testing of the concrete from the sensor.

Each of the frame side bars (3) comprise a sleeve (48) that prevents the concrete from adhering to the frame side bars (3). Respectively, the top portion and the bottom portion are sealed to prevent intrusion into their cavities. This is to allow the compression and force from the cylinder and the piston plate (42) to move, and to impact the strain gauge (8). Thus, several features are utilized including the felt washer (59), the first O-ring (61), the sealing ring (63), and the central O-ring (62), which are on both the top and base portions of the device.

The piston plate (42) is engaged by the air or pneumatic cylinder (43) to apply a known force, just as with FIG. 2A. Indeed, the measurement and function of each of the embodiments is virtually identical, with some of the features of FIG. 2B embodiment being required for larger dimension devices, because the weight of the concrete within the device becomes so significant that a precompression mechanism such as the spring is not sufficient to maintain the forces upon the strain gauge.

The relative position of these forces is easily understood when viewing FIGS. 3A and 3B. Specifically, FIG. 3B indicates a centralized circle, which is indicating the position of the strain gauge (8) positioned on the bottom internal face (20) of the bottom frame end plate (2). FIG. 3A details the top frame end plate (1) various position of several of the fasteners (10 and 4), as well as the waterproofing components (12) for the dry cavity (11).

In certain embodiments, the sensor comprises two or three frame side bars (3), which serve as rails along the longitudinal axis. In certain embodiments, within the dry cavity (11) is located the piston assembly (19) comprising the piston (5), the piston transfer component (6) and the piston transfer plate (7), and the compression mechanism (9). Typically, the precompression mechanism (9) is a spring or flexible elastomer, or as with the alternative embodiment, can be set with a screw or the movement of the piston. Positioned within the frame side bars (3), and inside of the intrusion cavity (22) is positioned the displacement measurement gauge (8). In preferred embodiments, the displacement measurement gauge (8) is a vibrating wire strain gage (VWSG) and comprises associated pressure hose (13) and sensor activation element (14) in order for both the piston (5) and the displacement measurement gauge (8) to function. The sensor, in its ultimate state, is intended for embedment within a fluid material prior to curing or hardening and, thus, the piston and compression spring must be housed within a fluid-tight cavity.

Numerous challenges were overcome during development to enable appropriate function of the sensor. Primary considerations included minimizing frictional effects associated with piston activation, minimizing load seating effects, and decoupling measurements from the effects of external load and time-dependent material shrinkage.

Bearing connection between the piston transfer component (6) and the piston transfer plate (7) allows for the piston transfer plate (7) to remain bonded to the sample material/VWSG, while the piston assembly (19) can retract, and it therefore isolates the displacement measurement gauge (8) from reading from potential effects of outside axial stresses along the longitudinal sensor direction. This detail also allows for troubleshooting and/or resetting of the piston (5) without disturbing the bond of the piston transfer plate (7) to the concrete. This allows for a remote retraction of the piston (5) from the piston transfer plate (7).

The precompression mechanism (9), for example, a spring, extends the piston during gage assembly and ensures gage axial equilibrium when unloaded, and induces an initial precompression within the displacement measurement gauge (8) to reduce seating effects between the displacement measurement gauge (8) and the piston transfer plate (7), upon piston activation. This can also be completed with the preload screw adjuster (46) during initial gage assembly.

The waterproofing materials (12 and 18) allow for sealing of the dry cavity (11). This provides a fluid-tight seal for this dry cavity (11). Furthermore, it enables small amounts of movements of the piston transfer plate (7) with minimum friction losses and assists in providing zero return during assembly and after piston (5) activation. Similarly, the inclusion of the O-rings (61 and 62) as well as the felt washer (59) aid in preventing concrete intrusion into the device. Those of ordinary skill in the art will recognize that in any movable element, a seal such as an O-ring is necessary to prevent the concrete from entering the cavity of the device and to allow for the movement of the device for testing purposes.

The frame side bars (3) need to be debonded from the hardened concrete within the gage. This allows the material sample to undergo longitudinal time-dependent shrinkage without restraint from rails and enable intended operation of the self-reacting frame. Similarly, the displacement measurement gauge (8) can have debonding at the surface, which allows material sample to undergo longitudinal time-dependent shrinkage without restraint from VWSG and facilitates measurement of material shrinkage (since last measurement) upon piston activation. As one of ordinary skill in the art understands, concrete shrinks with time, as, for example, a wet sponge shrinks as it dries. Thus, as the concrete shrinks, it closes in on itself. Where the concrete is bonded to something rigid, it cannot shrink. The device is created to allow for the concrete to shrink, and thus there is no bond created between the concrete and the rails. Thus, we used a "debonding" element, for example, grease, mylar film, a tubing surrounding the rails, etc. These prevent bonding with the rails themselves, which is necessary to allow the shrinkage of the concrete. For example, FIG. 2B details a sleeve (48) which prevents the bonding.

Turning now to FIG. 4, detailed are the operations of the sensor when embedded within hardened material sample. FIG. 4 details the conceptual operation of an embedded sensor (a) before activation at time $t=t_0$, (b) after shrinkage at time $t=t_1$, (c) and after activation at some later age, $t_2$.

At time $t=t_0$, FIG. 4A shows a partially embedded sensor before piston activation and before the start of any time-dependent material shrinkage (if applicable). Shortly thereafter at time $t=t_1$, unrestrained material shrinkage has begun, and the hardened material sample within the prototype is expected to exhibit a net shortening strain along the longitudinal gage length of the prototype. In FIG. 4B, this net dimensional decrease is denoted as shortening deformations, $\delta_1$ and $\delta_2$, idealized with half the total shortening deformation at the translating plate interface and the other half at the stationary plate interface. The true location of these shortening deformations is irrelevant as long as they occur within the gage length of the debonded vibrating wire strain gage. Upon piston activation (FIG. 4C), the middle plate initially translates toward the material sample a distance $\delta_1+\delta_2$ with minimal resistance as the waterproofing detail deforms and, upon contacting the hardened material sample, the piston applies a net compressive force. The exact three-dimensional distribution of induced stresses within the hardened material sample remains unknown, however finite element computer modeling suggests compressive force may engage a larger hardened material sample cross section near the middle of the gage length than at the ends due to shear deformations within the hardened material sample and the presence of the vibrating wire coil assembly within the gage length. Upon piston deactivation, the piston assembly returns to its original position without restraint from the adjacent translating plate due to the compression-compression interface detail as shown in FIGS. 3A and 3B.

Component Selection and Sizing for Concrete Applications

This section describes the appropriate sizing of prototype sensor components for the measurement of concrete modulus of elasticity. Although the component selection and sizing process is expected to differ for other materials, a similar procedure as outlined here may be useful for other future applications.

To ensure consolidation of concrete during placement, the American Concrete Institute (ACI) recommends that the minimum clear spacing between obstructions within concrete be limited to the greater of 1 in., the width of the obstruction, or 1.33 times the nominal maximum aggregate diameter. For a typical concrete aggregate diameter of 0.75 in., a minimum clear spacing for concrete flow of approximately 1.0 in. is appropriate. A sensor arrangement with a circular plate diameter of 4.0 in. and rail diameter of ⅜ in. was selected to meet this sizing requirement.

For measurement of induced shortening strains within the sensor gage length, a vibrating wire strain gage (VWSG) was selected for its durability and time stability. A VWSG measures concrete strain by recording the resonant frequency of a plucked wire that is tensioned between two flanges. The selected commercially available strain gage relies on an approximately 6.0 in. gage length to provide an advertised measurement accuracy of up to ±3.0 microstrain and a resolution which may vary based on the readout or the particular strain gauge, typically 1 microstrain. Bench testing conducted on vibrating wire strain gages affirmed that actual sensor accuracy and resolution exceeded the minimum advertised values. A vibrating wire reader/logger is required to provide excitation for the sensor, measure the resonant frequency.

With the sensor outer diameter and measurement gage length tentatively defined, planning considerations for the piston assembly proceeded. Hardened concrete, being a stiff material, requires a relatively large induced compressive stress to produce a corresponding measurable shortening strain. The piston selection process balanced the need to maximize applied force with the need for a reliable and inexpensive sacrificial component that would fit within the sensor diametric footprint. For the prototype sensor, a 150-psi pneumatic piston with a piston bore diameter of 1.5 in. was selected. This piston was able to exert a maximum force of 266 lb., neglecting frictional losses. However, subsequent designs have utilized pistons having a maximum force of greater than 3600 lb., with a preferred range of 1500-5000 lbs. in an about 6 in. sensor. These can be modified based on the size of the piston, the necessary force, and the material (the stress induced needs to be held within the linear elastic range), and thus the value can be significantly higher for larger devices. Such larger devices can actuate a larger footprint or volume of concrete. Those of ordinary skill in the art will recognize that the device can be manufactured with a pneumatic piston of appropriate size to exert and appropriate force.

Figure 5:
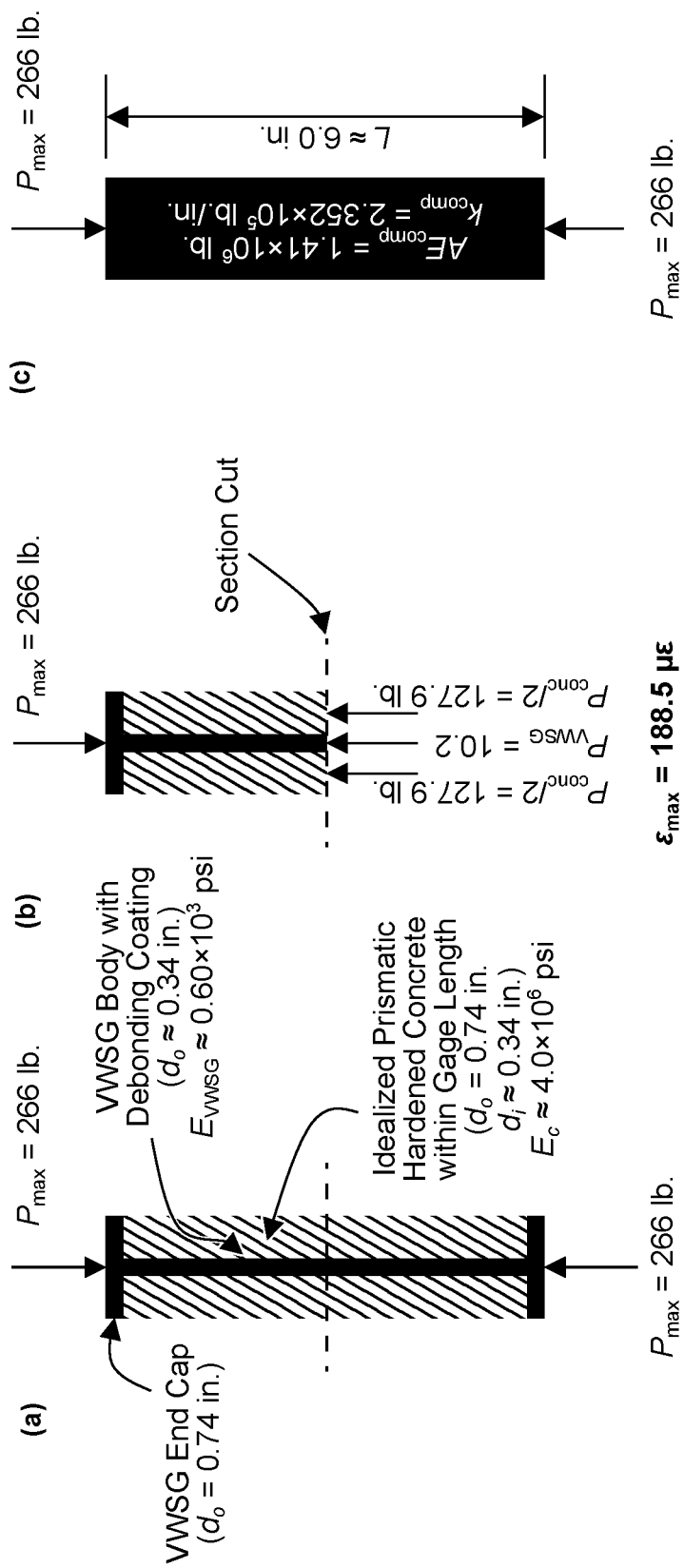
FIG. 5 details diagrams of derivation for hardened material samples.

To maximize sensor resolution, it was necessary to ensure that a measurable shortening strain would be induced by the anticipated applied force. Because the applied force was relatively small, the force was deliberately concentrated on the exterior of the 0.74 in. diameter end cap of the VWSG. This arrangement results in a compressive stress at the interface between the piston and the VWSG of approximately 618 psi. As the net force is applied to the VWSG end cap as shown in FIG. 5A, the cap acts as a rigid plate and distributes the force within the body of the VWSG and the surrounding hardened concrete sample in accordance with the relative axial stiffness of each component. Note that the nomenclature $d_o$ and $d_i$ refer to the outer and inner diameter, respectively, of a component.

The distribution of forces is governed by equilibrium and compatibility as shown in Equations 1 and 2, respectively.

$$P_{conc} + P_{VWSG} = 266 \text{ lb.} \quad \text{(Eq. 1)}$$

$$\varepsilon_c = \varepsilon_{VWSG}, \frac{P_{conc}}{A_{conc}E_c} = \frac{P_{VWSG}}{A_{VWSG}E_{VWSG}} \quad \text{(Eq. 2)}$$

Where:
$P_{conc}$=the internal force within the hardened concrete sample;
$P_{VWSG}$=the internal force within the tubular VWSG body;
$\varepsilon_c$=the shortening strain induced in the hardened concrete sample;
$\varepsilon_{VWSG}$=the shortening strain induced in the tubular VWSG body;
$A_{conc}$=the cross-sectional area of an idealized prismatic hardened concrete sample;
$A_{VWSG}$=the total cross-sectional area of the tubular VWSG body; and
$E_{VWSG}$=the modulus of elasticity of the tubular VWSG body.

For these calculations, the hardened material sample was assumed to be a prismatic core and the effective modulus of elasticity of the VWSG was provided by the manufacturer and also validated by bench testing. As shown in FIG. 5B, approximately 256 lb. of the hypothetical maximum 266 lb. applied load is transferred within the idealized prismatic concrete section, while approximately 10 lb. is expected to be carried within the tubular body of the much less stiff VWSG itself. The maximum concrete stress, $\sigma_{conc}$, and strain, $\varepsilon_{conc}$, expected to be induced within a typical hardened concrete sample with a modulus of elasticity of 4,000,000 psi is predicted in accordance with the following expressions:

$$\sigma_{conc} = \frac{P_{conc}}{A_{conc}} = \frac{255.8 * \text{lb.}}{\frac{\pi}{4}((0.74 * \text{in.})^2 - (0.34 * \text{in.})^2)} = 754 \text{ psi} \quad \text{(Eq. 3)}$$

$$\varepsilon_{conc} = \frac{P_{conc}}{A_{conc}E_{conc}} = \quad \text{(Eq. 4)}$$

$$\frac{255.8 * \text{lb.}}{\frac{\pi}{4}[(0.74 * \text{in.})^2 - (0.34 * \text{in.})^2](4.0(10)^6) * \text{psi}} = 188.5 \text{ microstrain}$$

The predicted concrete compressive stress, $\sigma_{conc}$, for the prototype sensor arrangement remains well below the proportional limit for typical hardened concrete, while the predicted concrete compressive strain, $\varepsilon_{conc}$, well exceeds the advertised precision of the selected vibrating wire strain gage. FIG. 5C illustrates a combined (composite) cross section that jointly represents the contribution of the VWSG tubular body and hardened concrete sample within an idealized prismatic sample. The effective axial stiffness, expressed both as a product of AE (lb.) and as k (lb./in.), was computed and is reported in FIG. 5C for use in subsequent design of the prototype sensor self-reacting frame.

To avoid potentially compromising prototype sensor resolution, the self-reacting frame assembly was designed with an axial stiffness that exceeded the axial stiffness of the idealized composite prismatic specimen detailed in FIG. 5C. Primary sources of anticipated axial deformation within the self-reacting frame were (i) longitudinal deformations of the rail assemblies during piston activation and (ii) the potential for differential bending between sensor stationary and translating plates that might compromise sensor resolution. Various arrangements of sensor prototype geometry and loadings were modeled in a finite element analysis (FEA) software to predict the anticipated structural response during piston activation, as shown in FIG. 6A.

The final arrangement utilized plate thicknesses of ½ in. for the stationary top frame end plate (1), ⅜ in. for the translating plate, and ⅞ in. for stationary plate (2) in the embodiment of FIG. 2A. In creating models, an exaggerated structural response of a sensor with both the left- and right-most plates fixed against axial deformation, and a similar analysis can be performed with the right-most plate permitted to deform in the sensor longitudinal direction. In these analytical models, the VWSG and concrete within are idealized as a compression spring with the net axial stiffness of $2.532 \times 10^5$ lb./in. as computed in FIG. 5C.

The results of such analytical models validate the device by predicting a measured shortening strain within the 6.0 in. gage length of approximately 193 microstrain as compared to the 188.5 microstrain computed in Eq. 4. In the hypothetical case of permitting axial translation at the right-most plate, the centroidal nodes of the right-most plate undergo an axial translation resulting from the combination of axial deformations of the rails and three-dimensional plate bending. Here, the predicted shortening strain within the 6.0 in. gage length is predicted from the net deformation of $1.154 \times 10^3$ in. and corresponds to a predicted strain of approximately 192 microstrain. The negligible difference between the analytical models having a fixed and free element affirm that the trial sizes of the self-reacting frame members are not expected to appreciably compromise sensor measurement potential. Further FEA analysis iterations suggested that any expected deformations in the right-most plate are largely self-compensating within the prototype sensor because additional piston travel and additional translation of the translating plate preserves the VWSG measurement gage length.

Among the most error-prone assumptions implicit to the above analyses is likely neglecting the presence of seating effects that are unavoidable on intermittently contacting surfaces. Initial validation experiments demonstrated that load seating effects were most pronounced upon initial contact of adjacent surfaces and their influence waned as load transfer progressed. To minimize the effects of seating within the sensor prototype and to simplify sensor fabrication, a compression spring was specified within the self-reacting frame assembly to subject the VWSG to a precompression during gage assembly. In FIG. 2A, the spring was sized such that the inner diameter was sufficient to surround the piston and the shortening during gage assembly would induce a precompression within the VWSG of approximately 5.0 lb. The small precompression was specified to ensure that the VWSG would not buckle prior to concrete placement and any associated strain shift within the VWSG would not cause the strain measurements to approach the VWSG lower measurement limit specified by the manufacturer. However, the particular weight and stiffness of the spring will depend on the particular load of concrete within the device and thus can be sized as necessary by those of ordinary skill in the art.

FIG. 2B provides an alternative embodiment, as detailed above. In certain embodiments, the weight of the concrete placed within the frame could have overwhelmed a flexible spring and resulted with improper control of strain gauge operating length. The weight of concrete within the gauge is about 7-8 lbs., and such weight may be beyond the ability of a flexible spring to control displacement to better than 0.001 in. In larger embodiments, as the size increases, so too would the weight. Therefore, the design was changed to make the top and bottom plates rigid so as not to be affected by concrete placement, and the piston transfer plate is buried beneath the strain gauge and rigid frame plate. There is no precompression element on the piston, and there is no requirement to keep the piston in contact with the strain gauge during casting. Notably, further seals keep out concrete. The adjustable preload screw element within the frame top plate provides for extremely good control over strain gauge mounting and initial preload of the gauge itself. Thus, depending on the particular embodiment, different mechanisms can be utilized to allow for initial preload of the strain gauge.

Pressurization of the sensor pneumatic piston relied on a source of 200 psi compressed air, an analog precision air regulator, and a digital high accuracy air pressure gage with an advertised resolution of 0.1 psi. Throughout the laboratory iterations of this project, the pneumatic system was refined to improve the stability of the compressed air supply.

Relying on the advertised resolution of each sensor component, an uncertainty analysis was performed to compute a hypothetical maximum anticipated measurement resolution for the prototype sensor. Any systematic offsets between the repeated readings of a prototype component and the true value (i.e., the accuracy of a component) were planned to be addressed by sensor calibration to known results and, thus, were not considered in this uncertainty analysis. The predictions of a hypothetical maximum sensor prototype measurement resolution presented here assume an average $E_c$ of approximately 4,000,000 psi and neglect the potential effects of load spreading within the hardened concrete material sample, frictional losses at various interfacing surfaces, and seating effects not overcome by the spring precompression. The pneumatic system of the prototype sensor regulates to a maximum pressure of 150 psi with a minimum resolution of 0.1 psi, which corresponds to a maximum stress within the idealized hardened concrete sample of 754 psi with a corresponding resolution of 0.50 psi. The vibrating wire strain gage is expected to measure a maximum strain of 0.0001885 in./in. with a minimum resolution of 0.000001 in./in. The above component measurement capabilities, when propagated to the computed parameter of modulus of elasticity, correspond to a predicted measurement of 4,000,000 psi with a resolution of approximately 24,000 psi or 24 ksi, offering promise to generate $E_c$ measurements meeting the reporting precision (50 ksi) of ASTM C469 [3]. Notably, the 754 psi is at the lower end of the maximum stress for the $f'_c$ of the material. Thus, a higher test may include a range from $0.0$-$0.6f'_c$ loaded to stress levels and preferably within the range of $0.25$-$0.5$ $f'_c$. Using the entire range of the applicable stress level allows the device to overcome limitations including: frictional contributions, volume of loaded concrete and relationship to aggregate size, making best use of linear elastic range of material so as to collect the most useful measurements for estimating modulus.

Laboratory Implementation

To demonstrate the feasibility of the sensor design, a sensor was fabricated and partially embedded within concrete. The sensor was monitored for 28 days and then disassembled to confirm intended operation.

Concrete Mixture and Hardened Properties

Figure 6:
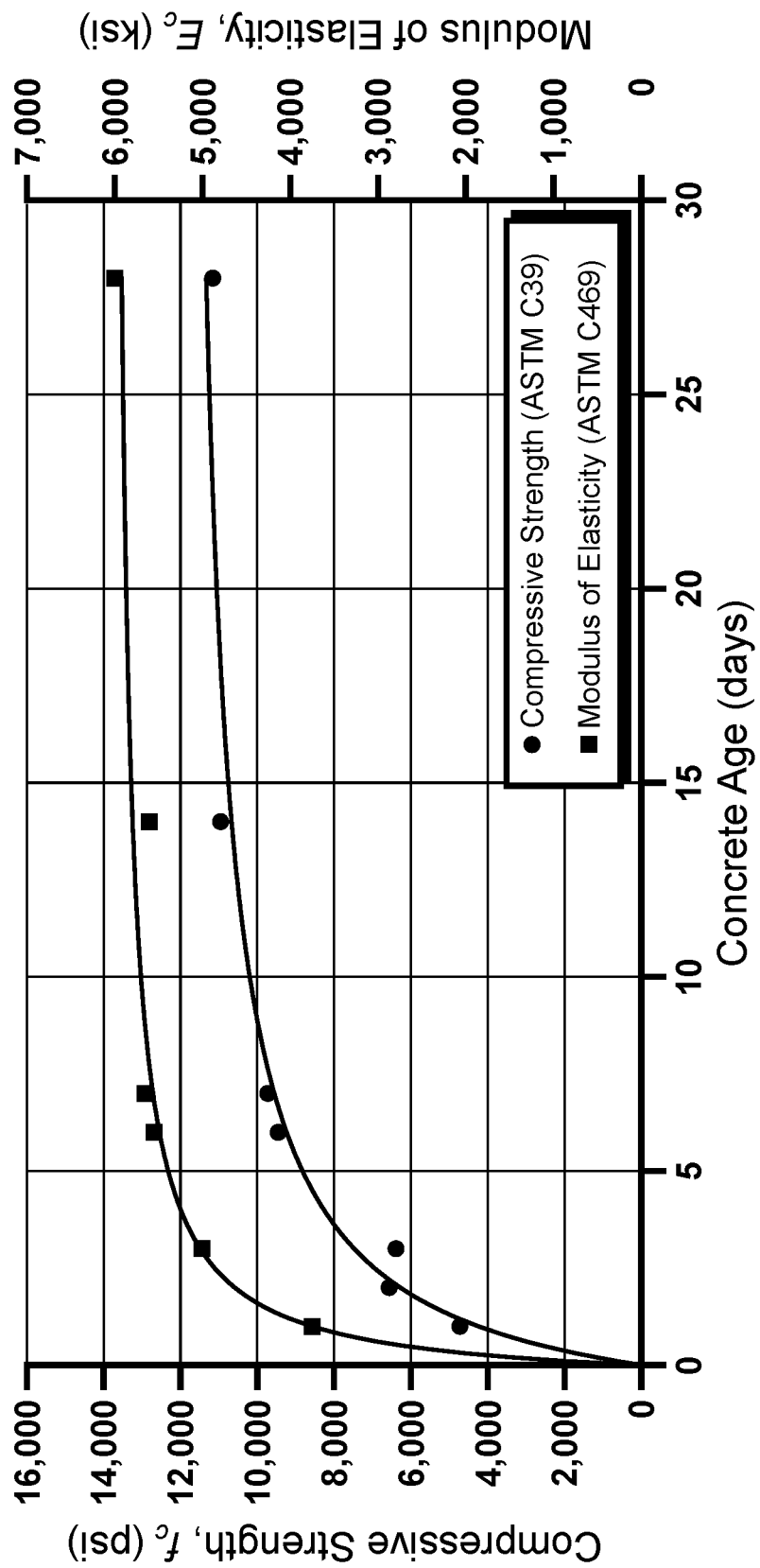
FIG. 6 details a graphical representation of concrete compressive strength and modulus of elasticity growth with time.

A concrete mixture with a target compressive strength of 11,000 psi was selected for use in a validating experiment. By validating the functionality of the sensor in a relatively strong and stiff concrete, it was expected that the sensor would also function properly for concretes that were weaker and less stiff. The mixture was characterized by a ratio of water-to-cementitious materials (by weight) of 0.36 and a highly workable concrete with a slump of 9 in. Destructive laboratory testing was conducted on companion hardened concrete 6 in.×12 in. cylinders to determine the time variation of the compressive strength, $f'_c$, and the modulus of elasticity, $E_c$, in accordance with ASTM C39 and ASTM C469, respectively. The experimental results for these parameters, as shown in FIG. 6, serve as best known measurements for the concrete mixture utilized in this study.

Figure 7:
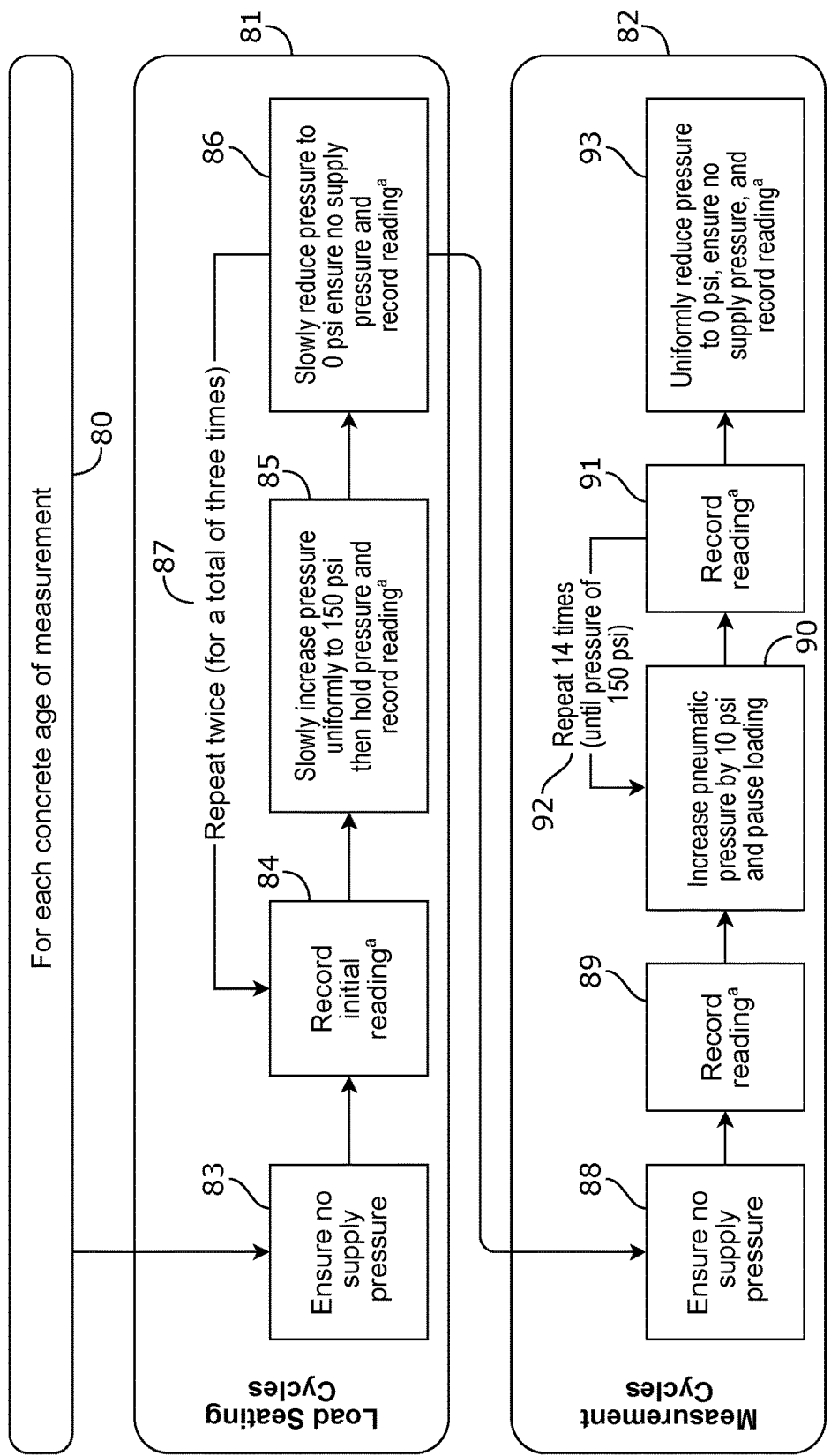
FIG. 7 details a sensor data collection protocol.

FIG. 7 details a data collection protocol, for each concrete age of measurement (80). There is a load seating cycle (81) which begins with ensuring no supply pressure (83), recoding of the initial reading (84), increasing the pressure to a uniform 150 psi and recording a reading (85), reducing the pressure back to 0 psi to ensure no supply pressure and recording a reading (86) and repeating this process two additional times (87). In the measurement cycles (82) (from step [86]), the process is to ensure no supply pressure (88), recording the reading (89), increasing pneumatic pressure by 10 psi and pause the loading (90), recording a reading (91), and repeating this step 14 times until a pressure of 150 psi is reached (92). This is done to slowly and evenly increasing the pressure and to collect data at each incremental pressure increase. Finally, when completed, the process uniformly reduces the pressure to 0 psi and ensures no supply pressure (93). Notably, as indicated in the figure, when a sensor reading is taken, the strain is measured along with the temperature to ensure accuracy and consistency as temperatures change.

Figure 8:
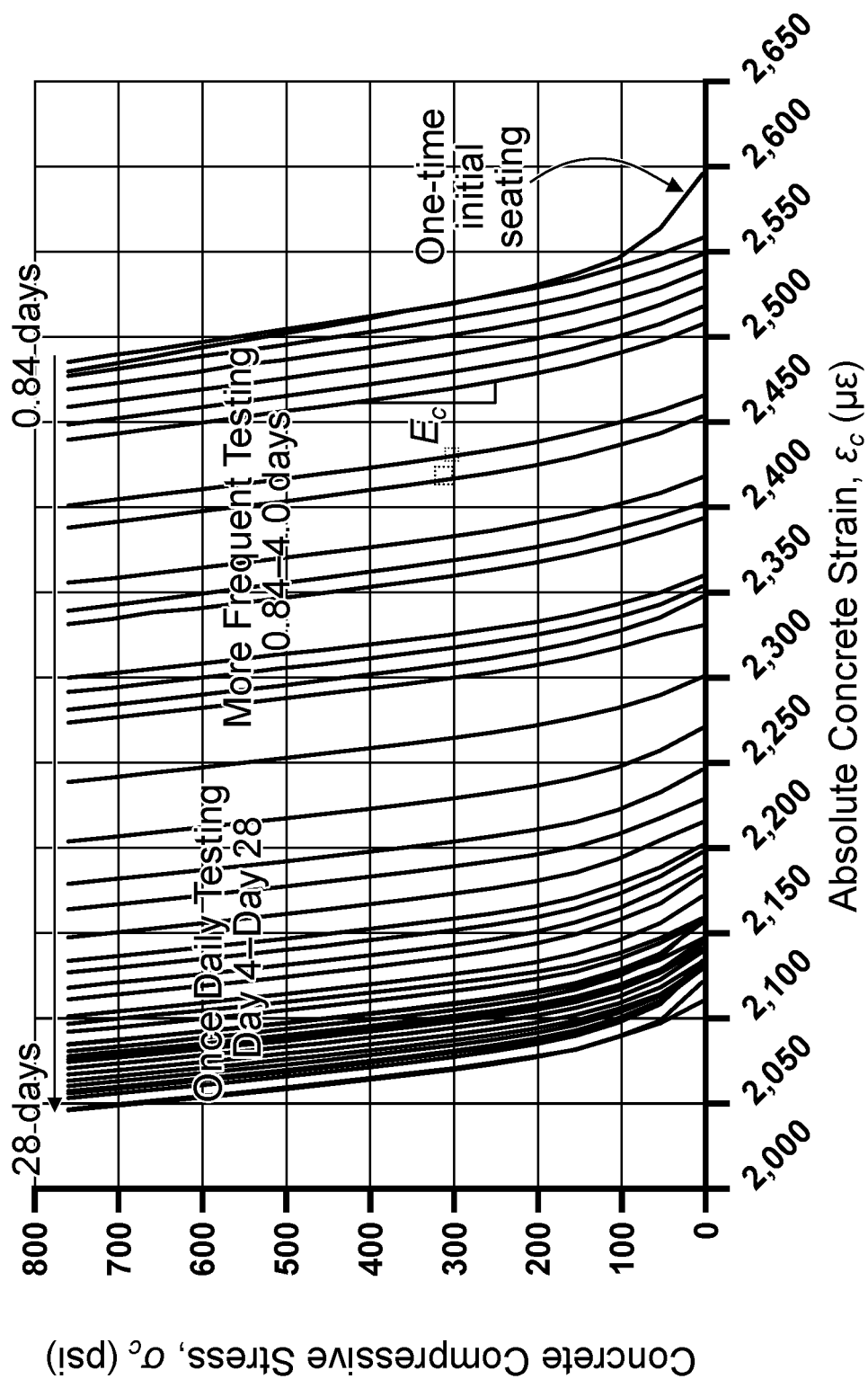
FIG. 8 details a graph showing sensor stress readings during loading.

To facilitate future comparisons between sensor readings and the companion cylinder tests of FIG. 8 at ages other than those of companion cylinder testing, a regression analysis was performed for each parameter. The compressive strength growth curve was generated in accordance with the recommendations of ACI 209R by appropriate calibration of curve fitting constants ($\alpha$=1.70 days and $\beta$=0.92 days), while the modulus of elasticity growth curve was generated by a Least Squares Regression Line of the data.

EXPERIMENTAL PROCEDURE

A fully assembled sensor was partially enclosed within a formwork of embodiment detailed in FIG. 2A. Fresh concrete was prepared and placed within the sensor through the access slot. Concrete was mechanically vibrated to ensure consolidation within the volume between the translating plate and the stationary plate. After placement, the sensor assembly was subjected to moist curing conditions until form removal. During concrete placement, concrete cylinders were also prepared for companion testing of compressive strength and modulus of elasticity. The sensor formwork was removed shortly after the ASTM C39 compressive strength testing on companion concrete cylinders affirmed that concrete strength exceeded the maximum anticipated stress that would be induced on the concrete by the sensor. After formwork removal, the specimen was stored in ambient laboratory conditions for the remainder of the testing period.

Sensor piston activation and corresponding data recording began at 0.84 days after concrete placement and continued through the age of 28 days after placement. Because modulus of elasticity tends to increase most rapidly during early ages, the frequency of data collection was maximized during the first three days of sensor monitoring. After this initial period, measurements were collected daily. Each measurement was recorded on the loading stroke of the piston in accordance with the data collection protocol detailed in FIG. 7.

During initial sensor monitoring, the importance of recording measurements consistently on the piston loading stroke became apparent. It was observed that if an operator unintentionally exceeded a target pressure (e.g., 135 psi instead of 130 psi) and then bled pressure to remedy the mistake, the recorded data was unreliable due to piston hysteresis.

At 28 days after concrete placement, the sensor was disassembled and inspected ensure intended performance including (i) adequate debonding between the rails and the adjacent concrete and (ii) ample consolidation of concrete within the intended material sample core.

EXAMPLES

Experimental Results

Sensor loading curves are shown for each age of concrete measurement in FIG. 8. The horizontal axis reflects absolute concrete strain, $\varepsilon_c$, while the vertical axis reports compressive stress induced by the piston, neglecting losses, at the concrete interface (up to 754 psi as computed from Eq. 3). Because concrete tends to undergo a time-dependent reduction in dimension due to moisture loss (i.e., shrinkage) as it matures, the time series of recorded strain data is read from right to left.

Each loading cycle is characterized by a nonlinear deformational response at small, induced stresses and a distinctly linear response thereafter. The observed initial nonlinear response for each loading event agrees with the hypothesized sensor behavior detailed in FIG. 4, both in its presence and its tendency to increase in relative magnitude as a function of time (as total shrinkage strain increases). The linear portion of each loading curve represents the proportional deformational response resulting from induced stress, i.e., the modulus of elasticity. Without postprocessing of the raw data, it is not possible to make direct observations on the relative magnitude of the modulus of elasticity among measurements.

Analysis of Results

Data Post Processing

Figure 9:
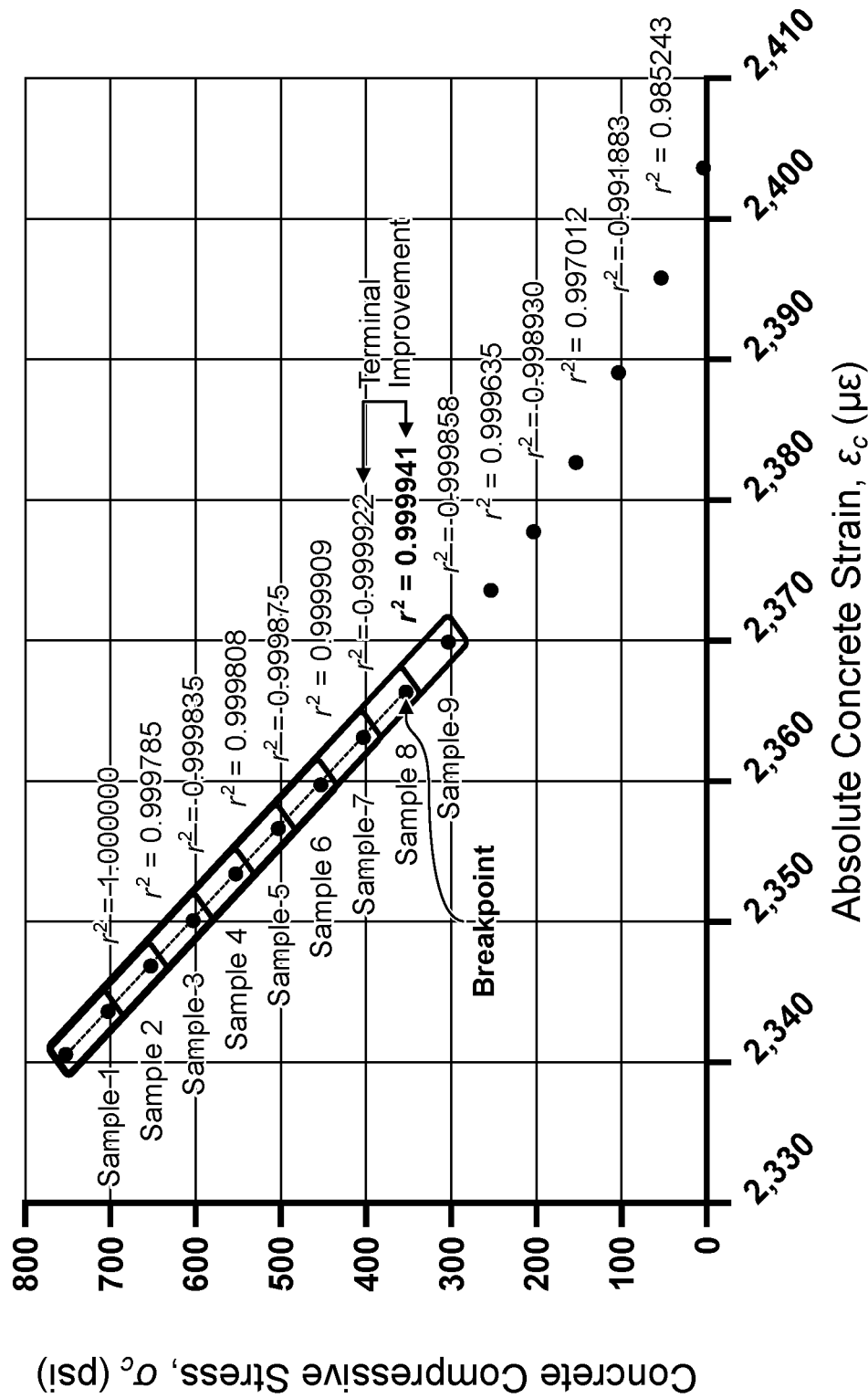
FIG. 9 details effect of stress-strain nonlinearity on linear regressions of sensor data.

Each raw measurement curve obtained from the prototype sensor required postprocessing to remove initial nonlinearities and to characterize the slope of the linear portion. A standardized analysis method was implemented to perform an appropriate regression that incorporated only the linear portion of each curve. This analysis method relied on identifying the point where the linear portion and the nonlinear portion of a load curve meet, hereafter referred to as the breakpoint. For illustrative purposes, the loading curve from day 2.25 is isolated in FIG. 9.

Each loading curve consists of 16 discrete measurement points recorded at increments of 50.3 psi of induced concrete compressive stress. For each curve, the recorded data was grouped into 15 samples, each containing one more point than its antecedent. Sample 1 contained the data collected between an induced concrete stress of 703.7 and 754 psi (corresponding to pneumatic pressures of 140 and 150 psi). The next grouping, Sample 2 in this case, added one additional data point and contained data collected between an induced concrete stress of 653.7 and 754 psi (corresponding to pneumatic pressures of 130 and 150 psi). Each subsequent grouping included an additional data point until the entirety of the load range was represented by Sample 15. Then, linear regression was performed for each of 15 samples, and their respective coefficients of determination were calculated using the following equation [10]:

$$r^2 = \frac{\sum_{i=1}^{n}(\varepsilon_i - \overline{\varepsilon})^2 - \sum_{i=1}^{n}(\varepsilon_i - \varepsilon_{pi})^2}{\sum_{i=1}^{n}(\varepsilon_i - \overline{\varepsilon})^2} \quad \text{(Eq. 5)}$$

Where:
- $r^2$=the coefficient of determination of a linear regression;
- n=the number of stress-strain points within a sampling group;
- $\varepsilon_i$=the strain measured for data point i;
- $\bar{\varepsilon}$=the mean strain measured within the sampling group; and
- $\varepsilon_{pi}$=the strain predicted for data point i by the linear regression.

To locate the terminal point on the linear portion of each curve (i.e., the breakpoint), the coefficient of determination for sampled groups containing at least three points were analyzed in descending order beginning with the sample with the least data (i.e., 130-150 psi). Note that the population for 140-150 psi was not considered as a candidate breakpoint, because the coefficient of determination was always equal to 1.0 for this interval. The point of terminal improvement in the coefficient of determination was designated as the breakpoint. For the 2.25-day series shown in FIG. 9, the terminal improvement in $r^2$ occurs between Sample 7 and Sample 8. The inclusion of one additional data point, represented by Sample 9, corresponded to a reduction in the coefficient of determination. No further increases in the coefficient of determination were observed for any remaining analyzed sample groupings. For the data series of FIG. 9, the slope of the best fit line of Sample 8 represents the modulus of elasticity for this age of measurement.

The foregoing postprocessing methodology was applied to the raw stress-strain data for each age of measurement to locate the breakpoint and subsequently determine Ec. The resulting time series of modulus of elasticity measurements was then calibrated to best match the ASTM C469 testing data for the concrete mixture used in this laboratory experiment. A single calibration coefficient was determined by minimizing the mean squared error, MSE (expressed as a percent) between the ASTM C469 testing results and the measurements generated from the prototype sensor, as adapted from ACI Committee 209 [11]:

$$MSE = \sqrt{\frac{\sum_{k=1}^{n}\left[\frac{100(E_{si} - E_{mi})}{E_{mi}}\right]^2}{n-1}} \quad \text{(Eq. 6)}$$

Where:
- n=the number of concrete modulus of elasticity values estimated by a sensor;
- $E_{si}$=the concrete modulus of elasticity estimated by a sensor, ksi; and
- $E_{mi}$=the concrete modulus of elasticity measured by ASTM C469 testing.

Figure 10:
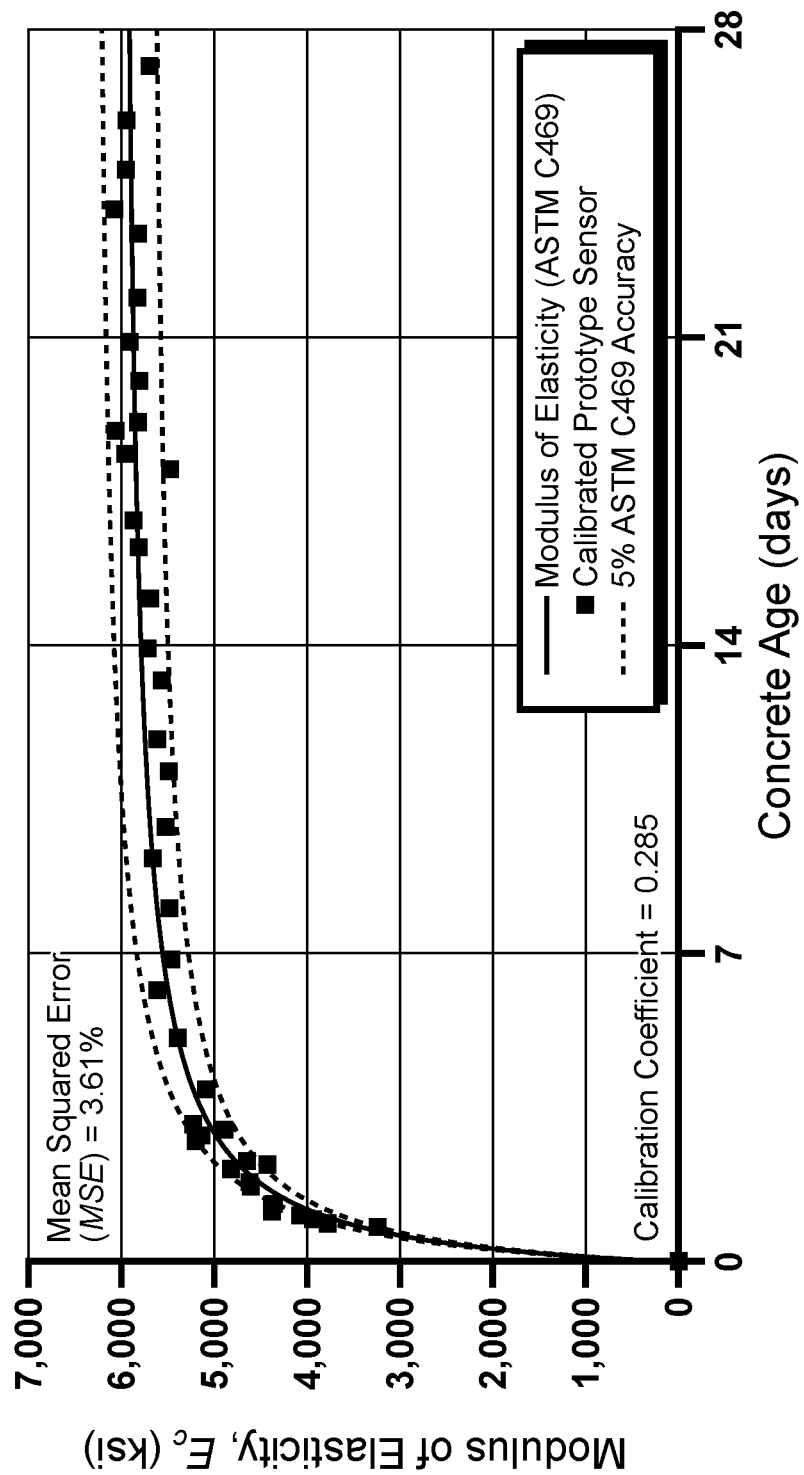
FIG. 10 details a comparison of modulus of elasticity measurements by a sensor of the present disclosure as compared to ASTM C469 testing.

Best fit of the sensor prototype data to the ASTM C469 data was achieved using a calibration coefficient of 0.285. The calibrated data for the prototype sensor is plotted in FIG. 10 with each data point representing the slope of an individual loading curve above the breakpoint.

ASTM C469 [3] states that "the results of tests of duplicate cylinders from different (concrete) batches should not depart more than 5% from the average of the two." As this testing specification is currently the accepted method for measuring concrete static modulus of elasticity, it is intuitive to compare the percent deviation of the sensor data from the measured ASTM C469 modulus of elasticity curve. For reference, the ±5% metric is superimposed on the data within FIG. 10.

Discussion of Results

Prototype Sensor Accuracy

The time-dependent concrete modulus of elasticity data obtained from the calibrated prototype sensor shows close agreement with the ASTM C469 test results for the concrete mixture utilized in this study. Of the 44 sensor prototype measurements, all but five are within the ±5% banding shown in FIG. 10. The average percent difference between the sensor measurements and ASTM C469 data for all measurements is approximately 0.2%, with 20 measurements falling below and 23 measurements above the ASTM C469 data. Of those measurements below and above the ASTM C469, respectively, the average percent differences were +3.28% and −2.49%. These average metrics of difference between sensor measurement and ASTM C469 were within the reporting precision of the ASTM C469 test procedure. As compared to the high stiffness concrete used in this study, it is expected that the sensor prototype accuracy will further improve for more common low-to-moderate stiffness concretes that will exhibit increased straining under the same imposed stress. However, it is unclear at this stage if the empirical calibration factor of 0.285 will directly apply to implementations of the sensor prototype in other concrete mixtures and will thus likely be modified based on the geometry of each device and the sensor utilized therein.

Concrete Shrinkage

From the raw sensor stress-strain data collected at varying concrete ages of FIG. 8, one can observe that there is a negative shift in strain (contraction) associated with the zero-stress point between subsequent dates that decreases in magnitude as the concrete age increases. This shift is indicative of concrete shrinkage, a phenomenon that tends to occur most rapidly in early concrete life and slows thereafter [9]. Neglecting the initial seating observed during first measurement at 0.84 days, the net decrease in observed unloaded strain within the 28-day monitoring window was approximately 430 microstrains. If not properly decoupled from sensor prototype measurements, the much larger magnitude of the shrinkage strain (430 microstrains) as compared to the strain induced by the piston during each loading cycle (up to 189 microstrains from Eq. 4) has the potential to compromise sensor functionality.

ACI 209R [9] suggests concrete shrinkage at time t, $(\varepsilon_{sh})_t$ can be predicted by:

$$(\varepsilon_{sh})_t = (\gamma_{cp})\left(\frac{t}{35+t}\right)(\varepsilon_{sh})_u \quad \text{(Eq. 7)}$$

Where:
- $\gamma_{cp}$=a factor for concrete moist curing during a period other than 7 days, =1.2 for moist curing duration of 1 day; and
- $(\varepsilon_{sh})_u$=ultimate shrinkage strain, =780 microstrain for typical concrete composition.

Substituting t=28 days, Eq. 7 predicts a net shrinkage strain of 415 microstrain at 28 days. The relative similarity between the predicted and observed shrinkage strain during the 28-day testing period suggests that the sensor prototype details, as implemented, were effective in isolating measurements from any major compromising influence of concrete shrinkage.

CONCLUSIONS

The following conclusions are supported by the work described in this study:

For concrete ages through 28 days, the calibrated prototype sensor generated modulus of elasticity measurements in agreement with ASTM C469 testing performed on the same concrete mixture.

Approximately 90% of calibrated prototype sensor measurements (39 of 44) were within a ±5% difference from companion ASTM C469 testing.

Of the 20 calibrated prototype sensor measurements that were less than indicated by companion ASTM C469 testing, the average underestimate was −2.49%.

Of the 23 calibrated prototype sensor measurements that were greater than indicated by companion ASTM C469 testing, the average overestimate was +3.28%.

A calibration factor of 0.285 provided the best agreement between raw prototype sensor measurements and ASTM C469 companion testing results. Further testing reveals that the geometry of the gauge and interactions with the concrete will modify this factor, such that a given size or specific sensor will differ from another sensor of a different size. It is not known if this factor is appropriate for prototype sensor implementations in other concrete mixtures or concrete immersion arrangements; and the sensor prototype appropriately characterized 28-day concrete shrinkage and successfully isolated time-dependent modulus of elasticity measurements from this simultaneous and potentially compromising phenomenon.

An additional potential application of the sensor detailed here is for the measurement of in situ creep. Creep is a material property relating to the continued (time-dependent) deformation of a material when subjected to an unchanging load. When loading is first applied, the specimen undergoes a corresponding shortening due to the loading. Then, if the applied load is maintained, the specimen undergoes further significant shortening deformation in the coming days, weeks, and years. Typically, creep testing of concrete is conducted in specialty laboratories in accordance with ASTM C512. Using this sensor, a user can actuate the piston with a certain pressure (to apply compressive stress to an in situ specimen) and maintain that pressure for the duration of the test (months or years). Various methods exist for maintaining pressure for an extended period of time including, but not limited to, accumulators and pressure control flow valves connected to a high-pressure reservoir. By maintaining the applied pressure to the piston within the sensor, it is possible to conduct an in situ creep test of concrete and/or other materials with significantly less effort than a laboratory test. Because creep testing in accordance with ASTM C512 also requires simultaneous measurement of concrete shrinkage, it is likely that additional displacement measurement gages (8) will need to be placed within the vicinity of the gage if the sensor described here is used for in situ creep measurement.

However, the ability of the device to remain in situ provides for new opportunities for development of continuous testing of concrete. Notably, the ability to continually test the material while it is first undergoing cure and then after it has cured to measure creep is complete unique. The prior art typically requires destruction of parallel samples to test the curing process and no reasonable methods exits to continuously test creep as is possible with the device.

REFERENCES

[1] Neville, A. M. 2013. *Properties of Concrete*. New Delhi, India: Dorling Kindersley.
[2] ASTM C39. 2020. *Standard Test Method for Compressive Strength of Cylindrical Concrete Specimens*. ASTM International. West Conshohocken, PA
[3] ASTM C469. 2014. *Standard Test Method for Static Modulus of Elasticity and Poisson's Ratio of Concrete in Compression*. ASTM International. West Conshohocken, PA
[4] Mante, D. M. 2019. "Measuring Concrete Modulus of Elasticity" *Concrete International*. Volume 41: Issue 8. Farmington Hills, MI: American Concrete Institute.
[5] ACI Committee 228. 2013. *Report on Nondestructive Test Methods for Evaluation of Concrete in Structures* (ACI 228.2R-13). Farmington Hills, MI: American Concrete Institute.
[6] Naaman, A. E. 2004. *Prestressed Concrete Analysis and Design: Fundamentals*. 2nd ed. Ann Arbor, MI: Techno Press 3000.
[7] ACI Committee 318. 2019. *Building Code Requirements for Structural Concrete* (ACI 318-19). Farmington Hills, MI: American Concrete Institute.
[8] Geokon. 2019. "Model 4200 Series Vibrating Wire Strain Gauges Instruction Manual." Document Revisions: DD. Lebanon, New Hampshire: Geokon.
[9] ACI Committee 209. 2008. *Prediction of Creep, Shrinkage, and Temperature Effects in Concrete Structures* (ACI 209R-92). Farmington Hills, MI: American Concrete Institute.
[10] Siegel, A. F. 2012. *Practical Business Statistics*. 6th Edition, 317. Burlington, MA: Elsevier Inc.
[11] ACI Committee 209. 2008. *Guide for Modeling and Calculating Shrinkage and Creep of Concrete* (ACI 209.2R-08). Farmington Hills, MI: American Concrete Institute.

What is claimed is:

1. A sensor device for detecting static modulus of elasticity in situ comprising:
    a top frame end plate and a bottom frame end plate, said top frame end plate and said bottom frame end plate connected by at least two frame side bars;
    a dry cavity connected to said top frame end plate, said dry cavity comprising a piston, and a piston transfer plate;
    a displacement measurement gauge extending from said dry cavity along a longitudinal axis of said sensor device, said displacement measurement gauge having a first end in contact with said piston transfer plate and a second end in contact with a bottom inner face of said bottom frame end plate; and
    a top inner face connected to said piston transfer plate, wherein a portion of elastomeric material is positioned on said bottom inner face and said top inner face, said elastomeric material positioned to prevent contact with either the bottom inner face or the top inner face except for a portion along the longitudinal axis of the displacement measurement gauge.

2. The sensor device of claim 1 further comprising a piston transfer component positioned between the piston and the piston transfer plate.

3. The sensor device of claim 1 further comprising a precompression mechanism.

4. The sensor device of claim 3 wherein said precompression mechanism is selected from the group consisting of: a spring, a threaded adjuster, a hydraulic piston, and combinations thereof.

5. The sensor device of claim 1 wherein said piston is a pneumatic, hydraulic, or mechanically driven remote actuated piston.

6. The sensor device of claim 1 wherein the elastomeric material is selected from the group consisting of: neoprene, silicone, rubber, foam, a compressible polymer, and combinations thereof.

7. The sensor device of claim 1 wherein the displacement measurement gauge is a vibrating wire strain gauge or a fiber optic sensor.

8. The sensor device of claim 1 wherein the piston provides a known force when actuated.

9. The sensor device of claim 1 further comprising a debonding material positioned on said at least two frame side bars.

10. A method of detecting static modulus of elasticity in situ from a structural component sample comprising:
   a. securing a sensor within a structural material;
   b. securing within said sensor between a top frame end plate and a bottom frame end plate a displacement measurement gauge along a longitudinal axis of said top frame end plate and said bottom frame end plate;
   c. activating a piston to a known force, said piston secured within a dry cavity attached to said top frame end plate wherein the piston extends from the top frame end plate to the bottom frame end plate along the longitudinal axis;
   d. measuring displacement of said sensor from said displacement measurement gauge; and
   e. calculating the static modulus of elasticity.

11. The method of claim 10 wherein the step of calculating the static modulus of elasticity further comprises:
   e1. plotting the displacement of said sensor against a set of data from a database that correlates results of in situ testing with ASTM results for different concrete compositions and strength levels.

12. The method of claim 11 wherein step (e1) comprises a Web-based data server, said Web-based data server automatically calculating and validating test data by comparing the test data to the set of data from a database.

13. The method of claim 10 wherein step (e) provides postprocessing of the displacement of said sensor as a curve of data, isolating a linear elastic portion of the curve, and calculating the modulus of elasticity.

14. The method of claim 10 comprising securing the sensor within a poured or cast structural material.

15. The method of claim 14 wherein the structural material is hardened.

16. The method of claim 14 wherein the structural material is concrete.

17. The method of claim 10 wherein the displacement measurement gauge is a vibrating wire strain gauge.

18. The method of claim 10 wherein the structural component sample is loaded to stress levels of between $0.0f'_c$ and $0.6f'_c$.

19. The method of claim 18 wherein the structural component sample is loaded to stress levels of between $0.25f'_c$ and $0.5f'_c$.

20. The method of claim 18 wherein measurement of in situ static concrete modulus of elasticity is repeatable within a single concrete sample.

* * * * *